(12) United States Patent
Hedrich et al.

(10) Patent No.: US 9,821,025 B2
(45) Date of Patent: Nov. 21, 2017

(54) HEMOSTATIC COMPOSITIONS

(71) Applicants: Baxter International Inc., Deerfield, IL (US); Baxter Healthcare S.A., Glattpark (Opfikon) (CH)

(72) Inventors: Hans Christian Hedrich, Vienna (AT); Joris Hoefinghoff, Vienna (AT); Katarzyna Gorna, Vienna (AT)

(73) Assignees: Baxter International Inc., Deerfield, IL (US); Baxter Healthcare, S.A., Glattpark (CH)

( * ) Notice: Subject to any disclaimer, the term of this patent is extended or adjusted under 35 U.S.C. 154(b) by 0 days.

(21) Appl. No.: 15/004,520

(22) Filed: Jan. 22, 2016

(65) Prior Publication Data

US 2016/0136235 A1 May 19, 2016

Related U.S. Application Data

(63) Continuation of application No. 13/648,902, filed on Oct. 10, 2012.

(60) Provisional application No. 61/545,909, filed on Oct. 11, 2011.

(51) Int. Cl.

| A61L 26/00 | (2006.01) |
|---|---|
| A61K 38/17 | (2006.01) |
| A61K 31/765 | (2006.01) |
| A61L 24/04 | (2006.01) |
| A61L 24/00 | (2006.01) |
| A61K 38/38 | (2006.01) |
| A61K 38/42 | (2006.01) |

(52) U.S. Cl.
CPC .......... *A61K 38/17* (2013.01); *A61K 31/765* (2013.01); *A61K 38/38* (2013.01); *A61K 38/42* (2013.01); *A61L 24/0031* (2013.01); *A61L 24/043* (2013.01); *A61L 26/008* (2013.01); *A61L 26/0052* (2013.01); *A61L 2400/04* (2013.01)

(58) Field of Classification Search
CPC ...... A61K 38/17; A61K 31/765; A61K 38/38; A61K 38/32; A61L 24/0031; A61L 24/043; A61L 26/0052; A61L 26/008; A61L 2400/04
See application file for complete search history.

(56) References Cited

U.S. PATENT DOCUMENTS

| 2,507,244 A | 5/1950 | Correll |
|---|---|---|
| 2,558,395 A | 6/1951 | Studer |
| 3,089,815 A | 5/1963 | Kupelwieser et al. |
| 4,006,220 A | 2/1977 | Gottlieb |
| 4,013,078 A | 3/1977 | Feild |
| 4,124,705 A | 11/1978 | Rothman et al. |
| 4,164,559 A | 8/1979 | Miyata et al. |
| 4,179,400 A | 12/1979 | Tsao et al. |
| 4,265,233 A | 5/1981 | Sugitachi et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,424,208 A | 1/1984 | Wallace et al. |
| 4,453,939 A | 6/1984 | Zimmerman et al. |
| 4,482,386 A | 11/1984 | Wittwer et al. |
| 4,515,637 A | 5/1985 | Cioca |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer |
| 4,600,574 A | 7/1986 | Lindner et al. |
| 4,640,834 A | 2/1987 | Eibl et al. |
| 4,655,211 A | 4/1987 | Sakamoto et al. |
| 4,746,514 A | 5/1988 | Warne |
| 4,749,689 A | 6/1988 | Miyata et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,885,161 A | 12/1989 | Cornell |
| 4,891,359 A | 1/1990 | Saferstein et al. |
| 4,925,677 A | 5/1990 | Feijen |
| 4,946,870 A | 8/1990 | Partain, III et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |

(Continued)

FOREIGN PATENT DOCUMENTS

| CN | 1270240 A | 10/2000 |
|---|---|---|
| EP | 0132983 A | 2/1985 |

(Continued)

OTHER PUBLICATIONS

"Carbonyl Fundamentals", 2006, author unknown, 8 pages.*

(Continued)

*Primary Examiner* — Karlheinz R Skowronek
*Assistant Examiner* — Joseph Fischer
(74) *Attorney, Agent, or Firm* — Kilpatrick Townsend & Stockton, LLP

(57) ABSTRACT

The invention discloses a hemostatic composition comprising:
a) a biocompatible polymer in particulate form suitable for use in hemostasis, and
b) one hydrophilic polymeric component comprising reactive groups.

14 Claims, 1 Drawing Sheet

(56) References Cited

U.S. PATENT DOCUMENTS

| | | |
|---|---|---|
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,569,193 A | 10/1996 | Hofstetter et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,658,592 A | 8/1997 | Tanihara et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,752,974 A | 5/1998 | Rhee et al. |
| 5,770,229 A | 6/1998 | Tanihara et al. |
| 5,853,749 A | 12/1998 | Hobbs |
| 5,856,356 A | 1/1999 | Tsouderos et al. |
| 5,861,043 A | 1/1999 | Carn |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,959,735 A | 9/1999 | Maris et al. |
| 5,997,895 A | 12/1999 | Narotam et al. |
| 6,063,061 A * | 5/2000 | Wallace ............. A61L 24/0015 424/423 |
| 6,066,325 A | 5/2000 | Wallace et al. |
| 6,110,484 A | 8/2000 | Sierra |
| 6,129,761 A | 10/2000 | Hubbell |
| 6,132,759 A | 10/2000 | Schacht et al. |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,458,147 B1 | 10/2002 | Cruise et al. |
| 6,458,386 B1 | 10/2002 | Schacht et al. |
| 6,458,889 B1 | 10/2002 | Trollsas |
| 6,495,127 B1 | 12/2002 | Wallace et al. |
| 6,624,245 B2 | 9/2003 | Wallace et al. |
| 6,706,690 B2 | 3/2004 | Reich et al. |
| 6,831,058 B1 | 12/2004 | Ikada et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 8,303,981 B2 | 11/2012 | Wallace et al. |
| 8,357,378 B2 | 1/2013 | Wallace et al. |
| 9,084,728 B2 * | 7/2015 | Goessl ............. A61K 9/0014 |
| 2002/0032463 A1 | 3/2002 | Cruise et al. |
| 2002/0165337 A1 | 11/2002 | Wallace et al. |
| 2002/0193448 A1 | 12/2002 | Wallace et al. |
| 2003/0064109 A1 | 4/2003 | Qian et al. |
| 2003/0129730 A1 | 7/2003 | Chenite et al. |
| 2004/0147465 A1 | 7/2004 | Jiang et al. |
| 2004/0214770 A1 | 10/2004 | Reich et al. |
| 2006/0004189 A1 | 1/2006 | Gandy |
| 2006/0105026 A1 * | 5/2006 | Fortune ............. A61L 15/225 424/443 |
| 2006/0147492 A1 | 7/2006 | Hunter et al. |
| 2006/0167561 A1 | 7/2006 | Odar et al. |
| 2006/0258560 A1 * | 11/2006 | Yang ............. A61L 24/043 514/17.2 |
| 2008/0085316 A1 | 4/2008 | Qian et al. |
| 2008/0091277 A1 | 4/2008 | Deusch et al. |
| 2008/0187591 A1 * | 8/2008 | Rhee ............. A61L 24/001 424/484 |
| 2008/0286376 A1 | 11/2008 | Qian et al. |
| 2009/0142396 A1 | 6/2009 | Odar et al. |
| 2010/0028309 A1 | 2/2010 | Odar et al. |
| 2010/0292717 A1 | 11/2010 | Petter-Puchner et al. |
| 2010/0318048 A1 | 12/2010 | Hoeffinghoff et al. |
| 2011/0046262 A1 | 2/2011 | Bublewitz et al. |
| 2012/0207813 A1 | 8/2012 | Rhee et al. |

FOREIGN PATENT DOCUMENTS

| | | |
|---|---|---|
| EP | 0282316 A2 | 9/1988 |
| EP | 0376931 | 7/1990 |
| EP | 0132983 B2 | 12/1991 |
| EP | 0493387 | 7/1992 |
| EP | 0891193 | 1/1999 |
| EP | 0612252 B1 | 5/1999 |
| EP | 1084720 A1 | 3/2001 |
| EP | 1283063 A1 | 2/2003 |
| EP | 1484070 A1 | 12/2004 |
| EP | 1414370 B1 | 4/2007 |
| JP | 51-125156 | 11/1976 |
| JP | 59-113889 | 6/1984 |
| JP | 05308969 | 11/1993 |
| JP | 6-254148 | 9/1994 |
| JP | 08-024325 | 1/1996 |
| JP | 9-504719 | 5/1997 |
| JP | 07090241 A | 4/2007 |
| KR | 10-1991-0007847 B1 | 10/1991 |
| WO | 86/00912 | 2/1986 |
| WO | 92/21354 | 12/1992 |
| WO | 92/22252 | 12/1992 |
| WO | 94/27630 A1 | 12/1994 |
| WO | 95/12371 | 5/1995 |
| WO | 95/15747 | 6/1995 |
| WO | 96/04025 | 2/1996 |
| WO | 96/06883 | 3/1996 |
| WO | 96/10374 | 4/1996 |
| WO | 96/10428 | 4/1996 |
| WO | 96/14368 | 5/1996 |
| WO | 96/39159 | 12/1996 |
| WO | 97/22371 | 6/1997 |
| WO | 97/37694 A1 | 10/1997 |
| WO | WO 97/44015 * 11/1997 ............... A61K 9/16 |
| WO | 98/08550 | 3/1998 |
| WO | 99/13902 A1 | 3/1999 |
| WO | 02/22059 A1 | 3/2002 |
| WO | 02/22184 A2 | 3/2002 |
| WO | 02/070594 A2 | 9/2002 |
| WO | 03/007845 | 1/2003 |
| WO | 2004/108179 A1 | 12/2004 |
| WO | 2006/031358 A | 3/2006 |

(56) References Cited

FOREIGN PATENT DOCUMENTS

| | | |
|---|---|---|
| WO | 2006/118460 A1 | 11/2006 |
| WO | 2007/001926 A2 | 1/2007 |
| WO | 2007/137839 A2 | 12/2007 |
| WO | 2007/137839 A3 | 12/2007 |
| WO | 2008/016983 A2 | 2/2008 |
| WO | 2013/053753 A2 | 4/2013 |
| WO | 2013/053755 A2 | 4/2013 |

OTHER PUBLICATIONS

A Universal Formulary, 1859, p. 393.*
Simulation of a continuous granular mixer: Effect of operating conditions on flow and mixing, Sarkar and Wassgren, Chemical Engineering Science 64 (2009) 2672-2682.*
Ansell et al., "Gelfoam and Autologous Clot Embolization: Effect on Coagulation." *Investigative Radiology* vol. 13 (1978): pp. 115-120.
Barrow, D.L., et al.; "The Use of Greater Omentum Vascularized Free Flaps for Neurosurgical Disorders Requiring Reconstruction." *Journal of Neurosurgery*, vol. 60 (Feb. 1984): pp. 305-311.
Barton, et al., "Fibrin Glue as a Biologic Vascular Patch—A Comparative Study." (abstract posted at http://www.ncbi.nlm.nih.gov/ on Jan. 3, 2001) *Journal Surgical Research* vol. 40.5 (1986): pp. 510-513.
Baxter product brochure for TissuFleece E, TissuCone E and TissuFoil E (2003).
Baxter Product Catalogue; Collagen; 4 pages (2006).
Baxter, "GentaFleece Collagen Fleece—Version 5 : Collagen Sponge with antibiotic protection for surgical use," Retrieved from http://www.advancingbiosurgery.com/en_EU/downloads/ifu_gentafleece.pdf, Mar. 2002, 2 pages. English portion second column of first page.
Boyers, et al., "Reduction of Postoperative Pelvic Adhesions in the Rabbit with Gore-Tex Surguical Membrane," *Fertility and Sterility* vol. 49.6 (1988): pp. 1066-1070.
Brett, David, A Review of Collagen and Collagen-based Wound Dressings, Wounds 2008;20(12).
Bruck, S. D., Ed., *Controlled Drug Delivery*. CRC Press, Boca Raton, FL (1983) A title page and table of contents.
Cantor, et al., "Gelfoam and Thrombin in Gastrointestinal Bleeding: An Experimental Study." (1950): pp. 890-893.
Cantor, et al., "Gelfoam and Thrombin in Treatment of Massive Gastroduodenal Hemmorhage: A Preliminary Report." *The American Journal of Surgery* (1950): pp. 883-887.
Cantor, et al., "Gelfoam and Thrombin in Treatment of Massive Upper Gastroduodenal Hemorrhage." *The American Journal of Surgery* (1951): pp. 230-235.
Chaplin, J.M., et al., "Use of an Acellular Dermal Allograft for Dural Replacement: An Experimental Study." *Neurosurgery* vol. 45.2 (Aug. 1999): pp. 320-327.
Chapter 10 of Biomaterials for Clinical Applications, Bhatia, pp. 213-258 Springer, 2010 (first available Aug. 23, 2010).
Cheung, David T., et al., "Mechanism of crosslinking of proteins by glutaraldehyde IV: In Vitro and In Vivo stability of a crosslinked collagen matrix." *Connective Tissue Research*, vol. 25.1 (1990): pp. 27-34.
Christensen, et al., "Qualitative Description of the Wurster-Based Fluid-Bed Coating Process." *Drug Development and Industrial Pharmacy* vol. 23.5 (1997): pp. 451-463.
Collins, et al., "Enemata of Gelfoam-Milk Suspension Combined with Thrombin Solution to Control Massive Hemorrhage Following Anorectal Surgery." *American Journal of Proctology* vol. 2 (1951): pp. 60-63.
Collins, Ronald et al., "Use of Collagen Film as a Dural Substitute: Preliminary Animal Studies." *Journal of Biomedical Materials Research* vol. 25 (1991): pp. 267-276.
D.J.S. Hulmes, Chapter 2, Collagen Diversity, Synthesis and Assembly, in Collagen Structure and Mechanics, Fratzl, P., Ed. 2008 Springer.

Edgerton, et al., "Vascular Hamartomas and Hemangiomos: Classification and Treatment." *Southern Medical Journal* vol. 75.12 (1982): pp. 1541-1547.
Filippi, R., et al., "Bovine Pericardium for Duraplasty: Clinical Results in 32 Patients." *Neurosurgical Review* vol. 20 (2001): pp. 103-107.
Gibble, et al., "Fibrin glue: the perfect operative sealant?" *Transfusion* vol. 30.8 (1990): pp. 741-747.
Guoping, Chen, et al., "Scaffold Design for Tissue Engineering." *Macromolecular Bioscience* (2002): pp. 67-77.
Heller, et al., "Release of Norethindrone from Poly(Ortho Esters)." *Polymer Engineering Science* vol. 21 (1981): pp. 727-731.
Hieb, Lee D., et al., "Spontaneous Postoperative Cerebrospinal Fluid Leaks Following Application of Anti-Adhesion Barrier Gel." *Spine* vol. 26.7 (2001): pp. 748-751.
Hood, et al., "Efficacy of Topical Hemostat Floseal Matrix in Vascular Surgery." 24th World Congress of the International Society for Cardiovascular Surgery (Sep. 12-16, 1999), 2 pages total.
Hotz, et al., "Collagen and Fibrin as Biologic Binders from Granular Hydroxyapatite." (abstract posted at http://www.ncbi.nlm.nih.gov/ on Jan. 3, 2001) *Dtsh. Z. Mund. Kiefer Geichtshir*. vol. 13.4 (1989): pp. 296-300.
International Search Report and Written Opinion dated Sep. 26, 2013 for PCT/EP2012/070061 filed Oct. 10, 2012, 13 pages.
Jeong, et al., "Biodegradable Block Copolymers as Injectible Drig-Delivery Systems." *Nature* vol. 388 (1997): pp. 860-862.
Jonas, Richard A., et al., "A new sealant for knitted Dacron prostheses: Minimally cross-linked gelatin." *Journal of Vascular Surgery* vol. 7.3 (1988): pp. 414-419.
Kim, Kee D., et al., "Reduction in Leg Pain and Lower-Extremity Weakness with Oxiplex/SP Gel for 1 Year after Laminectomy, Laminotomy, and Discectomy." *Neurosurgical Focus* vol. 17.1 (2004): pp. 1-6.
Kline, D.G., "Dural Replacement with Resorbable Collagen." *Archives of Surgery* vol. 91 (Dec. 1965): pp. 924-929.
Knopp, U., "A new collagen foil versus a cadaveric dura graft for dural defects—a comparative animal experimental study." EANS—12th European Congress of Neurosurgery, Lisbon (Sep. 7-12, 2003): pp. 663-666.
Kofidis, T., et al., "Clinically established Hemostatis Scaffold (Tissue Fleece) as Biomatrix in Tissue- and organ-engineering research." *Tissue Engineering* vol. 9.3 (2003): pp. 517-523.
Krill, et al., "Topical Thrombin and Powdered Gelfoam: An Efficient Hemostatic Treatment for Surgery." *Journal—Tennessee State Dental Association* vol. 66.2 (1986): pp. 26-27.
Kuhn, J., et al., "Bilateral Subdural Haemotomata and Lumbar Pseudomeningocele Due to a Chronic Leakage of Liquor Cerebrospinalis after a Lumbar Disectomy with the Application of ADCON-L Gel", *Journal of Neurology, Neurosurgery & Psychiatry* vol. 76 (2005): pp. 1031-1033.
Langer, et al., "Chemical and Physical Structure of Polymers as Carriers for Controlled Release of Bioactive Agents: A Review" *Journal of Macromolecular Science, Reviews on Macromolecular Chemistry and Physics* vol. C23.1 (1983): pp. 61-126.
Laquerriere, A., et al., "Experimental Evaluation of Bilayered Human Collagen as a Dural Substitute." *Journal of Neurosurgery* vol. 78 (1993): pp. 487-491.
Larson, Paul O., "Topical Hemostatic Agents for Dermatologic Surgery." *The Journal of Dermatologic Surgery and Oncology* vol. 14.6 (1988): pp. 623-632.
Le, A. X., et al., "Unrecognized Durotomy After Lumbar Discectomy: A Report of Four Cases Associated with the Use of ADCON-L." *Spine* vol. 26.1, (2001): pp. 115-118.
Lecut et al., Fibrillar type I collgens enhance platelet-dependent thrombin generation via glycoprotein VI with direct support of a2β1 but not allbβ3 integrin, Platelet and Blood Cells, 2005, pp. 107-114.
Lee, J.F., et al., "Experimental Evaluation of Silicone-Coated Dacron and Collagen Fabric-Film Laminate as Dural Substitutes." *Journal of Neurosurgery* vol. 27 (1967): pp. 558-564.
Leong, et al., "Polyanhydrides for Controlled Release of Bioactive Agents." *Biomaterials* vol. 7 (1986): pp. 364-371.
Leong, et al., "Polymeric Controlled Drug Delivery." *Advanced Drug Delivery Reviews* vol. 1 (1987): pp. 199-233.

(56) References Cited

OTHER PUBLICATIONS

Maok, "Hemostatic Agents." *Today's OR Nurse* vol. 13.11 (1991): pp. 6-10.
Maser, et al., "Synthesis of Polyurethanes and Investigation of their Hydrolytic Stability." *Journal of Polymer Science: Polymer Symposium* vol. 66 (1979): pp. 259-268.
Matsumoto, K., et al., "A Gelatin Coated Collagen-Polyglycolic Acid Composite Membrane as a Dural Substitute." *American Society for Artificial Internal Organs Journal* (2001): pp. 641-645.
Maurer, P.K., et al., "Vicryl (Polyglactin 910) Mesh as a Dural Substitute." *Journal of Neurosurgery* vol. 63 (Sep. 1985): pp. 448-452.
McClure, et al., "Massive Gastroduodenal Hemorrhage: Treatment with Powdered Gelfoam and Buffered Thrombin Solution." *Surgery* vol. 32 (1952): pp. 630-637.
McPherson, J. M., et al., "An examination of the biologic response to injectable, glutaraldehyde cross-linked collagen implants." *Journal of Biomedical Materials Research* vol. 20.1 (1986): pp. 93-107.
McPherson, J. M., et al., "The preparation and physiochemical characterization of an injectable form of reconstituted, glutaraldehyde cross-linked, bovine corium collagen." Journal of Biomedical Materials Research vol. 20.1 (1986): pp. 79-92.
McPherson, John M., et al., "The Effects of Heparin on the Physiochemical Properties of Reconstituted Collagen." *Collagen and Related Research* vol. 8.1 (1988): pp. 65-82.
Meddings, N., et al., "Collagen Vicryl—A New Dural Prosthesis," *Acta Neurochir.* vol. 117 (1992): pp. 53-58.
Mello, L.R., et al., "Duraplasty with Biosynthetic Cellulose: An Experimental Study." *Journal of Neurosurgery* vol. 86 (Jan. 1997): pp. 143-150.
Narotam, P.K., et al., "A Clinicopathological Study of Collagen Sponge as a Dural Graft in Neurosurgery." *Journal of Neurosurgery* vol. 82 (Mar. 1995): pp. 406-412.
Narotam, P.K., et al., "Experimental Evaluation of Collagen Sponge as a Dural Graft." *British Journal of Neurosurgery* vol. 7 (1993):pp. 635-641.
Nektar Advanced PEGylation 2005-2006 Catalog, Nektar Therapeutics, 2005.
Nimni, M. E., et al., "Chemically modified collagen: A natural biomaterial for tissue replacement." *Journal of Biomedical Materials Research* vol. 21.6 (1987): pp. 741-771.
Nimni, Marcel E., "The cross-linking and structure modification of the collagen matrix in the design of cardiovascular prosthesis." *Journal of Cardiac Surgery* vol. 3.4 (1988): pp. 523-533.
O'Neill, P., et al., "Use of Porcine Dermis as Dural Substitute in 72 Patients." *Journal of Neurosurgery* vol. 61 (Aug. 1984): pp. 351-354.
Palm, S.J., et al., "Dural Closure with Nonpenetrating Clips Prevents Meningoneural Adhesions: An Experimental Study in Dogs." *Neurosurgery* vol. 45.4 (Oct. 1999):pp. 875-882.
Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochir* vol. 139 (1997): pp. 827-838.
Park, Y-K., at al., "Prevention of Arachnoiditis and Postoperative Tethering of the Spinal Cord with Gore-Tex Surgical Membrane: An Experimental Study with Rats," *Neurosurgery* vol. 42.4 (Apr. 1998): pp. 813-824.
PCT International Preliminary Report on Patentability, International Search Report and Written Opinion dated Feb. 17, 2009, International Application No. PCT/US2007/074984, 8 pages.
Pietrucha, K., "New Collagen Implant as Dural Substitute." *Biomaterials* vol. 12 (Apr. 1991): pp. 320-323.
Pitt, et al., *Controlled Release of Bioactive Materials*. Ed. R. Baker, New York: Academic Press, 1980.
Porchet, Francois, "Inhibition of Epidural Fibrosis with ADCON-L: Effect on Clinical Outcome One Year Following Re-operation for Recurrent Lumbar Radiculopathy." 1998, pp. 1-10.

Raul, J.S., et al.; "Utilisation du Polyester Urethane (NEUROPATCH®) Comme Substitut Dural"; Neurochirugie; vol. 49:2-3; pp. 83-89 (2003), English abstract only on p. 83.
Raul, J.S., et al., "Utilisation du Polyester Urethane (NEUROPATCH®) Comme Substitut Dural." *Neurochirugie* vol. 49.2-3 (2003): pp. 83-89. English abstract only on p. 83.
Reddy, M., et al., "A Clinical Study of a Fibrinogen-Based Collagen Fleece for Dural Repair in Neurosurgery." *Acta Neurochirugie* vol. 144 (2002): pp. 265-269.
Riley, et al., "Percutaneous Liver Biopsy with Plugging of Needle Track: A Safe Method for Use in Patients with Impaired Coagulation." *Lancet* (Aug. 25, 1984): p. 436.
Rosenblatt, Joel, et al., "Effect of electrostatic forces on the dynamic rheological properties of injectable collagen biomaterials." *Biomaterials* vol. 13.12 (1992): pp. 878-886.
Rosenblatt, Joel, et al., "Injectable collagen as a pH-sensitive hydrogel." *Biomaterials* vol. 15.12 (1994): pp. 985-995.
Ross, Jeffrey S., et al., "Association Between Peridural Scar and Recurrent Radicular Pain After Lumbar Discectomy: Magnetic Resonance Evaluation." *Neurosurgery* (1996): pp. 855-863.
Rossler, B., et al., "Collagen microparticles: preparation and properties." *Journal of Microencapsulation* vol. 12.1 (Jan.-Feb. 1995): pp. 49-57.
San-Galli, F., et al., "Experimental Evaluation of a Collagen-Coated Vicryl Mesh as a Dural Substitute." *Neurosurgery* vol. 30.3 (1992): pp. 396-401.
Shaffrey, C.I., et al., "Neurosurgical Applications of Fibrin Glue: Augmentation of Dural Closure in 134 Patients." *Neurosurgery* vol. 26.2 (1990): pp. 207-210.
Sidman, et al., "Biodegradable, Implantable Sustained Release Systems Based on Glutamic Acid Copolymers." *Journal of Membrane Science* vol. 7 (1979): pp. 227-291.
Smith, K. A., et al., "Delayed Postoperative Tethering of the Cervical Spinal Cord." *Journal of Neurosurgery* vol. 81 (Aug. 1994): pp. 196-201.
Springorum, H.W., "Die Verwendung von Kollagenfolien zur Uberbruckung von Defekten des Gleitgewebes bei Achillotenotomien und Achillessehnenrupturen." *Akt. Traumata.* vol. 15 (1985): pp. 120-121. English abstract only on p. 120.
Stricker, A., et al., "Die Verwendung von TissuFoil Membran bei der Sinusbodenaugmentation." *Ellipse* vol. 17.1 (2001): pp. 1-5. English abstract only on p. 1.
Sugitachi, et al., "A Newly Devised Chemo-embolic Agent, G.T. XIII-ADM." (English abstract posted at http://www.ncbi.nlm.nih.gov/ on Jan. 3, 2001) *Gan. To. Kagaku Ryoho*. vol. 12.10 (1985): pp. 1942-1943.
Sugitachi, et al., "Locoregional Therapy in Patients with Malignant Pleural Effusion—Two Different Kinds of BAC Therapy" (English abstract posted at http://www.ncbi.nlm.nih.gov/ on Jan. 3, 2001) *Gan. To. Kagaku Ryoho*. vol. 19.10 (1992): pp. 1640-1643.
Sugitachi, et al., "Preoperative Transcatheter Arterial Chemoembolization for Locally Advanced Breast Cancer: Application for New Thrombotic Materials." *The Japanese Journal of Surgery* vol. 13.5 (1 9 83): pp. 456-458.
TissuFleece E, Version 5, Package Leaflet, Baxter International Inc., 2003, 8 pages, *English portion of instructions for use*.
Tobin, et al., "Plugged Liver Biopsy in Patients with Impaired Coagulation." *Digestive Diseases and Science* vol. 34.1 (1989): pp. 13-15.
Tucker, et al., *Absorbable Gelatin (Gelfoam) Sponge*. Springfiled, Illinois: Charles T. Thomas, 1965, pp. 3-125.
Vander Salm, et al., "Reduction of Sternal Infection by Application of Topical Vancomycin." *Journal of Thoracic Surgery* vol. 98 (1989): pp. 618-622.
Vinas, F.E., et al., "Evaluation of Expanded Polytetrafluoroethylene (ePTFE) versus Polydioxanone (PDS) for the Repair of Dura Mater Defects." *Neurological Research* vol. 21 (Apr. 1999): pp. 262-268.
Wallace et al., "A Tissue Sealant Based on Reactive Multifunctional Polyethylene Glycol", J. Biomed Mater Res (Appl Biomater) 58:545-555, 2001.
Wallace, D. G., et al., "Injectable cross-linked collagen with improved flow properties." *Journal of Biomedical Materials Research* vol. 23.8 (Aug. 1989): pp. 931-945.

(56) References Cited

OTHER PUBLICATIONS

Wallace, Donald, "The relative contribution of electrostatic interactions to stabilization of collagen fibrils." *Biopolymers* vol. 29.6-7 (May-Jun. 1990): pp. 1015-1026.

Warren, W.L., et al., "Dural Repair Using Acellular Human Dermis: Experience with 200 Cases: Technique Assessment." *Neurosurgery* vol. 46.6 (Jun. 2000): pp. 1391-1396.

Yuki, et al., "Effects of Endoscopic Variceal Sclerotherapy using GT XIII on Blood Coagulation Tests and the Renal Kallikrein-kinin System." (English abstract posted at http://www.ncbi.nlm.nih.gov/ on Jan. 3, 2001) *Gastroenterology Japan* vol. 25.5 (1990): pp. 561-567.

Ziegelaar, B.W., et al., "The characterisation of human respiratory epithelial cells cultured on reabsorbable scaffolds: first steps towards a tissue engineered tracheal replacement." *Biomaterials* vol. 23 (2002): pp. 1425-1438.

Ziegelaar, B.W., "Tissue Engineering of a Tracheal Equivalent." Doctoral Thesis at Ludwig Maximilians University, Munich, Germany, 2004, 25 pages.

Zins, et al., "US-Guided Percutaneous Liver Biopsy with Plugging of the Needle Track: A Prospective Study in 72 High-Rish Patients." *Radiology* vol. 184.3 (1992): pp. 841-843.

\* cited by examiner

HEMOSTATIC COMPOSITIONS

CROSS-REFERENCES TO RELATED APPLICATIONS

This application is a continuation of U.S. patent application Ser. No. 13/648,902, filed on Oct. 10, 2012, and entitled "Hemostatic Compositions," which is a nonprovisional of and claims benefit under 35 USC 119(e) of U.S. Provisional Application No. 61/545,909, filed on Oct. 11, 2011, and entitled "Hemostatic Compositions," the entire disclosure of each of which is incorporated herein by reference for all purposes.

FIELD OF THE INVENTION

The present invention relates to hemostatic compositions and processes for making such compositions.

BACKGROUND OF THE INVENTION

Hemostatic compositions in dry storage-stable form that comprise biocompatible, biodegradable, dry stable granular material are known e.g. from WO98/008550A or WO 2003/007845A. These products have been successfully applied on the art for hemostasis. Floseal® is an example for a powerful and versatile hemostatic agent consisting of a granular gelatin matrix swollen in a thrombin-containing solution to form a flowable paste.

Since such products have to be applied to humans, it is necessary to provide highest safety standards for quality, storage-stability and sterility of the final products and the components thereof. On the other hand, manufacturing and handling should be made as convenient and efficient as possible.

On the other hand, it has been found that previous hemostatic compositions for wound healing failed to induce hemostasis at conditions with impaired hemostasis (e.g. after heparinization). It is therefore desired to provide materials and compositions with improved hemostasis. Moreover, a strong adherence of the compositions applied to the tissue is needed when the composition is applied to a wound. It is also desired to provide material with suitable swelling behavior after application to a wound.

It is an object of the present invention to overcome such problems and provide suitable hemostatic compositions with improved adhering properties and methods for making such hemostatic composition. The compositions should also be provided in a convenient and usable manner. The products should preferably be provided in product formats enabling a convenient provision of "ready-to-use" hemostatic compositions, which can be directly applied to an injury without any time consuming reconstitution steps.

SUMMARY OF THE INVENTION

Therefore, the present invention provides a hemostatic composition comprising:
a) a biocompatible polymer in particulate form suitable for use in hemostasis, and
b) one hydrophilic polymeric component comprising reactive groups.

The combination of a biocompatible polymer in particulate form with one hydrophilic polymeric component provides a composition with improved hemostatic properties and with improved tissue adherence. This is specifically suitable for wound treatment wherein induction of hemostasis failed, e.g. at conditions with impaired hemostasis (e.g. after heparinization). The compositions according to the present invention improve hemostasis. Furthermore, the compositions according to the present invention show a strong adherence to the tissue when applied to a wound.

Upon contact with bleeding tissue, a crosslinking reaction of the hydrophilic polymeric component with the blood proteins leads to formation of a gel with sealing and hemostatic properties. Crosslinking also occurs to the tissue surface proteins and, depending on the nature of the biocompatible polymer material, may also occur to the biocompatible polymer material. The latter reaction contributes to an improved adhesion of the composition material to the wounded tissue surface.

A further aspect relates to a method of treating an injury comprising administering a hemostatic composition to the site of injury.

Also provided is a kit for the treatment of an injury, comprising a hemostatic composition as herein disclosed and instructions for use.

The present invention also refers to a method for producing the hemostatic composition according to the invention in a convenient manner allowing the composition to be easily at hand for medical use. The invention further relates to a method for delivering a hemostatic composition to a target site in a patient's body, said method comprising delivering a hemostatic composition produced by the process of the present invention to the target site. According to another aspect, the present invention relates to a finished final container obtained by the process according of the present invention containing the present hemostatic composition. The invention also relates to a method for providing a ready-to-use hemostatic composition comprising contacting a hemostatic composition produced by the process of the present invention with a pharmaceutically acceptable diluent as well as to a kit comprising the finished final container and other means for applying the composition (e.g. a diluent container). The compositions according to the present invention are particularly useful for providing hemostasis at bleeding sites, including surgical bleeding sites, traumatic bleeding sites and the like. An exemplary use of the compositions may be in sealing the tissue tract above a blood vessel penetration created for vascular catheterization.

DESCRIPTION OF SPECIFIC EMBODIMENTS OF THE INVENTION

The present invention provides an improvement in hemostatic compositions. The hemostatic compositions according to the invention contain biocompatible polymers in particulate form, e.g. granules of a biocompatible polymer (e.g. gelatin, fibrin, chitosan, fibronectin, collagen, especially gelatin) suitable for use in hemostasis (the "hemostatic biocompatible polymer component" or the "hemostatic polymer. Admixed to this biocompatible polymer for hemostasis is one hydrophilic polymeric component comprising reactive groups. According to the present invention, the reactive groups of the polymeric component have retained their reactivity until the composition is brought to the place of clinical action, e.g. on to the wound.

The biocompatible polymers in particulate form suitable for use in hemostasis may include dimensionally isotropic or non-isotropic forms. For example, the biocompatible polymers according to the present invention may be granules or fibers; and may be present in discontinuous structures, for example in powder forms.

According to a preferred embodiment, the biocompatible polymer is liquid absorbing. For example, upon contact with liquids, e.g. aqueous solutions or suspensions (especially a buffer or blood) the polymer takes up the liquid and will display a degree of swelling, depending on the extent of hydration. The material preferably absorbs from about 200% to about 2000%, especially from about 400% to about 1300% water or aqueous buffer by weight, corresponding to a nominal increase in diameter or width of an individual particle of subunit in the range from e.g. approximately 50% to approximately 500%, usually from approximately 50% to approximately 250%. For example, if the (dry) granular particles have a preferred size range of 0.01 mm to 1.5 mm, especially of 0.05 mm to 1 mm, the fully hydrated composition (e.g. after administration on a wound or after contact with an aqueous buffer solution) may have a size range of 0.05 mm to 3 mm, especially of 0.25 mm to 1.5 mm.

The equilibrium swell of preferred biocompatible polymers of the present invention may generally range e.g. from 400% to 1300%, preferably being from 500% to 1100%, depending on its intended use. Such equilibrium swell may be controlled e.g. (for a crosslinked polymer) by varying the degree of crosslinking, which in turn is achieved by varying the crosslinking conditions, such as the type of crosslinking method, duration of exposure of a crosslinking agent, concentration of a crosslinking agent, crosslinking temperature, and the like. Materials having differing equilibrium swell values perform differently in different applications. For example, the ability to inhibit bleeding in a liver divot model was most readily achieved with crosslinked gelatin materials having a swell in the range from 700% to 950%. For a femoral artery plug, lower equilibrium swell values in the range from 500% to 600% were more successful. Thus, the ability to control crosslinking and equilibrium swell allows the compositions of the present invention to be optimized for a variety of uses. In addition to equilibrium swell, it is also important to control the hydration of the material immediately prior to delivery to a target site. Hydration and equilibrium swell are, of course, intimately connected. A material with 0% hydration will be non-swollen. A material with 100% hydration will be at its equilibrium water content. Hydrations between 0% and 100% will correspond to swelling between the minimum and maximum amounts.

According to a preferred embodiment of the present invention, the biocompatible polymer and the hydrophilic polymeric component are present in dry form, preferably in mixed dry form.

The biocompatible polymer in particulate form suitable for use in hemostasis of the present invention may be formed from biologic and non-biologic polymers. Suitable biologic polymers may contain a protein, a polysaccharide, a biologic polymer, a non-biologic polymer; and derivatives and combinations thereof. Suitable proteins include gelatin, collagen, albumin, hemoglobin, fibrinogen, fibrin, casein, fibronectin, elastin, keratin, and laminin; and derivatives and combinations thereof. Particularly preferred is the use of gelatin or soluble non-fibrillar collagen, more preferably gelatin, and exemplary gelatin formulations are set forth below. Other suitable biologic polymers include polysaccharides, such as glycosaminoglycans, starch, cellulose, dextran, hemicellulose, xylan, agarose, alginate and chitosan; and derivatives and combinations thereof. Suitable non-biologic polymers will be selected to be degradable by either of two mechanisms, i.e. (1) break down of the polymeric backbone or (2) degradation of side chains which result in aqueous solubility. Exemplary non-biologic biocompatible polymers suitable for use in hemostasis include synthetics, such as polyacrylates, polymethacrylates, polyacrylamides, polymethacrylamides, polyethyleneimines, polyvinyl resins, polylactide-glycolides, polycaprolactones, and polyoxyethlenes; and derivatives and combinations thereof. Also combinations of different kinds of polymers are possible (e.g. proteins with polysaccharides, proteins with non-biologic hydrogel-forming polymers, etc.). Preferred hemostatic polymers comprise amino-groups, specifically if the hydrophilic polymeric component has reactive groups which react with amino-groups upon administration (e.g. in the wound environment).

"A derivative thereof" includes any chemically modified polymer, such as e.g. a crosslinked polymer.

Preferred hemostatic polymers comprise nucleophilic groups, such as e.g. amino-groups, specifically if the hydrophilic polymeric component has reactive groups which react with amino-groups upon administration (e.g. in the wound environment).

According to a preferred embodiment of the present invention, the biocompatible polymer is selected from the group consisting of gelatin, collagen, albumin, fibrinogen, fibrin and derivatives thereof (as defined above); especially preferred the polymer is gelatin or collagen; especially preferred is crosslinked gelatin.

According to a preferred embodiment of the present invention, the biocompatible polymer suitable for use in hemostasis contains a crosslinked protein, a crosslinked polysaccharide, a crosslinked biologic polymer, a crosslinked non-biologic polymer; or mixtures thereof.

A non-crosslinked polymer may be crosslinked in any manner suitable to reconstitute, e.g. to form a suitable hydrogel base of the hemostatic polymer. For example, polymeric molecules may be crosslinked using bi- or poly-functional crosslinking agents which covalently attach to two or more polymer molecules chains. Exemplary bifunctional crosslinking agents include aldehydes, epoxides, succinimides, carbodiimides, maleimides, azides, carbonates, isocyanates, divinyl sulfone, alcohols, amines, imidates, anhydrides, halides, silanes, diazoacetate, aziridines, and the like. Alternatively, crosslinking may be achieved by using oxidizers and other agents, such as periodates, which activate side-chains or moieties on the polymer so that they may react with other side-chains or moieties to form the crosslinking bonds. An additional method of crosslinking comprises exposing the polymers to radiation, such as gamma radiation, to activate the polymer chains to permit crosslinking reactions. Dehydrothermal crosslinking methods may also be suitable. Preferred methods for crosslinking gelatin molecules are described below.

The biocompatible hemostatic polymer—once applied to a wound—forms an efficient matrix which can form a barrier for blood flow. Specifically the swelling properties of the hemostatic polymer can make it an effective mechanical barrier against bleeding and rebleeding processes.

In a preferred embodiment, the hemostatic compositions according to the present invention are provided or used as granular preparations. According to a preferred embodiment, the biocompatible polymer granulates suitable for use in hemostasis contain a crosslinked protein, a crosslinked polysaccharide, or a crosslinked non-biologic polymer; or mixtures thereof.

As mentioned above, the biocompatible polymer suitable for use in hemostasis is preferably a granular material. This granular material can rapidly swell when exposed to a fluid (i.e. the diluent) and in this swollen form is capable of contributing to a flowable paste that can be applied to a bleeding site. The biocompatible polymer, e.g. gelatin, may be provided as a film which can then be milled to form a granular material. Most of the particles contained in this granular material (e.g. more than 90% w/w) have preferably particle sizes of 10 to 1.000 µm, especially 50 to 700 µm.

According to a preferred embodiment, the biocompatible polymer in particulate form suitable for use in hemostasis is a crosslinked gelatin. Dry crosslinked gelatin powder can be prepared to re-hydrate rapidly if contacted with a pharmaceutically acceptable diluent. The gelatin granules, especially in the form of a gelatin powder, preferably comprise relatively large particles, also referred to as fragments or sub-units, as described in WO98/08550A and WO2003/007845A. A preferred (median) particle size will be the range from 10 to 1.000 µm, preferably from 50 to 700 µm, but particle sizes outside of this preferred range may find use in many circumstances. The dry compositions will also display a significant "equilibrium swell" when exposed to an aqueous re-hydrating medium (=diluents, also referred to as reconstitution medium or re-hydration medium). Preferably, the swell will be in the range from 400% to 1000%. "Equilibrium swell" may be determined by subtracting the dry weight of the gelatin hydrogel powder from its weight when fully hydrated and thus fully swelled. The difference is then divided by the dry weight and multiplied by 100 to give the measure of swelling. The dry weight should be measured after exposure of the material to an elevated temperature for a time sufficient to remove substantially all residual moisture, e.g., two hours at 120° C. The equilibrium hydration of the material can be achieved by immersing the dry material in a pharmaceutically acceptable diluent, such as aqueous saline, for a time period sufficient for the water content to become constant, typically for from 18 to 24 hours at room temperature.

Exemplary methods for producing crosslinked gelatins are as follows. Gelatin is obtained and suspended in an aqueous solution to form a non-crosslinked hydrogel, typically having a solids content from 1% to 70% by weight, usually from 3% to 10% by weight. The gelatin is crosslinked, typically by exposure to either glutaraldehyde (e.g., 0.01% to 0.05% w/w, overnight at 0° C. to 15° C. in aqueous buffer), sodium periodate (e.g., 0.05 M, held at 0° C. to 15° C. for 48 hours) or 1-ethyl-3-(3-dimethylaminopropyl) carbodiimide ("EDC") (e.g., 0.5% to 1.5% w/w overnight at room temperature), or by exposure to about 0.3 to 3 megarads of gamma or electron beam radiation. Alternatively, gelatin particles can be suspended in an alcohol, preferably methyl alcohol or ethyl alcohol, at a solids content of 1% to 70% by weight, usually 3% to 10% by weight, and crosslinked by exposure to a crosslinking agent, typically glutaraldehyde (e.g., 0.01% to 0.1% w/w, overnight at room temperature). In the case of aldehydes, the pH should be held from about 6 to 11, preferably from 7 to 10. When crosslinking with glutaraldehyde, the crosslinks are formed via Schiff bases which may be stabilized by subsequent reduction, e.g., by treatment with sodium borohydride. After crosslinking, the resulting granules may be washed in water and optionally rinsed in an alcohol, and dried. The resulting dry powders may then be provided in the final container as described herein.

Preferably, the biocompatible polymer is provided in a dry granular form for producing the hemostatic compositions according to the present invention. A "dry granular preparation of a biocompatible polymer" according to the present invention is known e.g. from WO 98/08550 A. Preferably, the polymer is a biocompatible, biodegradable dry stable granular material.

The dry polymer according to the present invention is usually provided with particle sizes of 10 to 1.000 µm. Usually, the polymer particles have a mean particle diameter ("mean particle diameter" is the median size as measured by laser diffractometry; "median size" (or mass median particle diameter) is the particle diameter that divides the frequency distribution in half; fifty percent of the particles of a given preparation have a larger diameter, and fifty percent of the particles have a smaller diameter) from 10 to 1000 µm, especially 50 to 700 µm (median size). Applying larger particles is mainly dependent on the medical necessities; particles with smaller mean particle diameters are often more difficult to handle in the production process. The dry polymer is therefore provided in granular form. Although the terms powder and granular (or granulates) are sometimes used to distinguish separate classes of material, powders are defined herein as a special sub-class of granular materials. In particular, powders refer to those granular materials that have the finer grain sizes, and that therefore have a greater tendency to form clumps when flowing. Granules include coarser granular materials that do not tend to form clumps except when wet. For the present application the particles used are those which can be coated by suitable coating techniques Particle size of the polymer granules according to the present invention can therefore easily be adapted and optimized to a certain coating technique by the necessities of this technique.

The hydrophilic polymeric component (also referred to as "reactive hydrophilic component" or "hydrophilic (polymeric) crosslinker") of the hemostatic composition according to the present invention is a hydrophilic crosslinker which is able to react with its reactive groups once the hemostatic composition is applied to a patient (e.g. to a wound of a patient or another place where the patient is in need of a hemostatic activity). Therefore it is important for the present invention that the reactive groups of the polymeric component are reactive when applied to the patient. It is therefore necessary to manufacture the hemostatic composition according to the present invention so that the reactive groups of the polymeric component which should react once they are applied to a wound are retained during the manufacturing process.

This can be done in various ways. For example, usual hydrophilic polymeric components have reactive groups which are susceptible to hydrolysis after contact with water. Accordingly, premature contact with water or aqueous liquids has to be prevented before administration of the hemostatic composition to the patient, especially during manufacture. However, processing of the hydrophilic polymeric component during manufacturing may be possible also in an aqueous medium at conditions where the reactions of the reactive groups are inhibited (e.g. at a low pH). If the hydrophilic polymeric components can be melted, the melted hydrophilic polymeric components can be sprayed or printed onto the matrix of the biopolymer. It is also possible to mix a dry form (e.g. a powder) of the hydrophilic polymeric component with a dry form of the biocompatible polymer suitable for use in hemostasis. If necessary, then an increase of the temperature can be applied to melt the sprinkled hydrophilic polymeric component to the biocompatible polymer suitable for use in hemostasis to achieve a permanent coating of the hemostatic composition. Alternatively, these hydrophilic polymeric components can be taken up into inert organic solvents (inert vis-à-vis the reactive groups of the hydrophilic polymeric components) and brought onto the matrix of the biomaterial. Examples of such organic solvents are dry ethanol, dry acetone or dry dichloromethane (which are e.g. inert for hydrophilic polymeric components, such as NETS-ester substituted PEGs).

The term "one hydrophilic polymeric component comprising reactive groups" means that the presence of a second or further hydrophilic polymeric component with nucleophilic reactive groups is excluded in a hemostatic composition according to the present invention.

In a preferred embodiment the hydrophilic polymer component is a single hydrophilic polymer component and is a polyalkylene oxide polymer, preferably a PEG comprising polymer. The reactive groups of this reactive polymer are preferably electrophilic groups.

The reactive hydrophilic component may be a multi-electrophilic polyalkylene oxide polymer, e.g. a multi-electrophilic PEG. The reactive hydrophilic component can include two or more electrophilic groups, preferably a PEG comprising two or more reactive groups selected from succinimidylesters (—CON(COCH$_2$)$_2$), aldehydes (—CHO) and isocyanates (—N=C=O), e.g. a component as disclosed in the WO2008/016983 A (incorporated herein by reference in its entirety) and one of the components of the commercially available ones under the trademark CoSeal®.

Preferred electrophilic groups of the hydrophilic polymeric crosslinker according to the present invention are groups reactive to the amino-, carboxy-, thiol- and hydroxy-groups of proteins, or mixtures thereof.

Preferred amino group-specific reactive groups are NETS-ester groups, imidoester groups, aldehyde-groups, carboxy-groups in the presence of carbodiimides, isocyanates, or THPP (beta-[Tris(hydroxymethyl)phosphino]propionic acid), especially preferred is Pentaerythritolpoly(ethyleneglycol)ether tetrasuccinimidyl glutarate (=Pentaerythritol tetrakis[1-1'-oxo-5'-succinimidylpentanoate-2-poly-oxoethyleneglycole]ether (=an NHS-PEG with MW 10,000).

Preferred carboxy-group specific reactive groups are amino-groups in the presence of carbodiimides.

Preferred thiol group-specific reactive groups are maleimides or haloacetyls.

Preferred hydroxy group-specific reactive group is the isocyanate group.

The reactive groups on the hydrophilic crosslinker may be identical (homofunctional) or different (heterofunctional). The hydrophilic polymeric component can have two reactive groups (homobifunctional or heterobifunctional) or more (homo/hetero-trifunctional or more).

In special embodiments the material is a synthetic polymer, preferably comprising PEG. The polymer can be a derivative of PEG comprising active side groups suitable for crosslinking and adherence to a tissue.

By the reactive groups the hydrophilic reactive polymer has the ability to crosslink blood proteins and also tissue surface proteins. Crosslinking to the biomaterial is also possible.

The multi-electrophilic polyalkylene oxide may include two or more succinimidyl groups. The multi-electrophilic polyalkylene oxide may include two or more maleimidyl groups.

Preferably, the multi-electrophilic polyalkylene oxide is a polyethylene glycol or a derivative thereof.

In a most preferred embodiment the hydrophilic polymeric component is pentaerythritolpoly(ethyleneglycol)ether tetrasuccinimidyl glutarate (=COH102, also pentaerythritol tetrakis[1-1'-oxo-5'-succinimidylpentanoate-2-poly-oxoethyleneglycole]ether).

The hydrophilic polymeric component is a hydrophilic crosslinker. According to a preferred embodiment, this crosslinker has more than two reactive groups for crosslinking ("arms"), for example three, four, five, six, seven, eight, or more arms with reactive groups for crosslinking. For example, NHS-PEG-NHS is an effective hydrophilic crosslinker according to the present invention. However, for some embodiments, a 4-arm polymer (e.g. 4-arms-p-NP-PEG) may be more preferred; based on the same rationale, an 8-arm polymer (e.g. 8-arms-NHS-PEG) may even be more preferred for those embodiments where multi-reactive crosslinking is beneficial. Moreover, the hydrophilic crosslinker according to the present invention is a polymer, i.e. a large molecule (macromolecule) composed of repeating structural units which are typically connected by covalent chemical bonds. The hydrophilic polymer component according to the present invention should have a molecular weight of at least 1000 Da (to properly serve as crosslinker in the hemostatic composition according to the present invention); preferably the crosslinking polymers according to the present invention has a molecular weight of at least 5000 Da, especially of at least 8000 Da.

For some hydrophilic crosslinkers, the presence of basic reaction conditions (e.g. at the administration site) is preferred or necessary for functional performance (e.g. for a faster crosslinking reaction at the administration site). For example, carbonate or bicarbonate ions (e.g. as a buffer with a pH of 7.6 or above, preferably of 8.0 or above, especially of 8.3 and above) may be additionally provided at the site of administration (e.g. as a buffer solution or as a fabric or pad soaked with such a buffer), so as to allow an improved performance of the hemostatic composition according to the present invention or to allow efficient use as a hemostatic and/or wound adherent material.

The reactivity of the hydrophilic polymeric component (which, as mentioned, acts as a crosslinker) in the composition according to the present invention is retained in the composition. This means that the reactive groups of the crosslinker have not yet reacted with the hemostatic composition and are not hydrolyzed by water (or at least not in a significant amount which has negative consequences on the hemostatic functionality of the present compositions). This can be achieved by combining the hemostatic polymer with the hydrophilic crosslinker in a way which does not lead to reaction of the reactive groups of the crosslinker with the hemostatic polymer or with water. Usually, this includes the omitting of aqueous conditions (or wetting), especially wetting without the presence of acidic conditions (if crosslinkers are not reactive under acidic conditions). This allows the provision of reactive hemostatic materials.

According to a specifically preferred hemostatic composition of the invention, the biocompatible polymer is crosslinked gelatin and the hydrophilic polymeric component is pentaerythritolpoly(ethyleneglycol)ether tetrasuccinimidyl glutarate.

Preferred ratios of the biocompatible polymer to hydrophilic polymeric component in the hemostatic composition according to the present invention are from 0.1 to 50% w/w, preferably from 5 to 40% w/w.

The hemostatic compositions according to the present invention are preferably provided as dry composition, e.g. as a physical mixture, of the hemostatic polymer and the hydrophilic reactive component, wherein the biocompatible polymer and the hydrophilic polymeric component are present in dry form, preferably in mixed dry form. "Mixed" according to the present invention includes powder mixing, coating, impregnating, blending, agglomerating, co-lyophilizing, drying from suspension, subsequent or concurrent co-filling, co-extruding, etc.

A "dry" hemostatic composition according to the present invention has only a residual content of moisture which may approximately correspond to the moisture content of comparable available products, such as Floseal® (Floseal, for example, has about 12% moisture as a dry product). Usually, the dry composition according to the present invention has a residual moisture content below these products, preferably below 10% moisture, more preferred below 5% moisture, more preferred below 2.5%, especially below 1% moisture. The hemostatic composition according to the present invention can also have lower moisture content, e.g. 0.1% or even below. Preferred moisture contents of the dry hemostatic composition according to the present invention are 0.1 to 10%, especially 0.5 to 5%. It is clear that the dryer the composition is, the longer their shelf life is and the lower is the risk that the hemostatic properties of the composition as a whole suffer.

As already stated, the biocompatible polymer in particulate form suitable for use in hemostasis is preferably gelatin in powder form, especially wherein the powder particles have a median particle size of 10 to 1000 µm, preferably from 50 to 750 µm, more preferred from 150 to 700 µm, especially from 150 to 500 µm.

Further components may be present in the hemostatic composition according to the present invention. According to preferred embodiments, the hemostatic compositions according to the present invention may further comprise a substance selected from the group consisting of antifibrinolytic, procoagulant, platelet activator, antibiotic, vasoconstrictor, dye, growth factors, bone morphogenetic proteins and pain killers.

The hemostatic composition according to the present invention may comprise a further composition of gelatin and a polyvalent nucleophilic substance, preferably human serum albumin, optionally at a basic pH (e.g. pH 8 to 11, preferably 9 to 10, especially at a pH of 9.5). The 2 components may then be co-applied to an injury.

According to another aspect, the present invention relates to the use of a hemostatic composition according to the present invention for the treatment of an injury selected from the group consisting of a wound, a hemorrhage, damaged tissue, bleeding tissue and/or bone defect.

The present invention also relates to a method of treating an injury selected from the group consisting of a wound, a hemorrhage, damaged tissue and/or bleeding tissue comprising administering a hemostatic composition according to the present invention to the site of injury.

According to another aspect, the present invention provides a kit for the treatment of an injury selected from the group consisting of a wound, a hemorrhage, damaged tissue and/or bleeding tissue comprising:

a) a hemostatic composition according to the present invention; and b) instructions for use.

The present invention also relates to a method for producing a hemostatic composition according to the present invention comprising the step of mixing, a biocompatible polymer suitable for use in hemostasis and one hydrophilic polymeric component comprising reactive groups in dry form.

It is preferred to provide the hemostatic compositions according to the present invention in dry form in an administration container, preferably in a syringe, optionally together with a pharmaceutically acceptable diluent.

These hemostatic compositions according to the present invention may be reconstituted to "ready-to-use" hemostatic preparations using pharmaceutically acceptable diluents (e.g. aqueous ionic solutions). Preferably, the "ready-to-use" preparations are present or provided as hydrogels. Products of this kind are known in principle in the art, yet in a different format: Usually, the components are provided as separate entities in dry form. Before mixing the components for administration to a patient, the dry components are usually contacted separately with pharmaceutically acceptable diluents. Mixing of the components is then performed by mixing the separately reconstituted components.

For stability reasons, such products (as well as the products according to the present invention) are usually provided in a dry form and brought into the "ready-to-use" form (which is usually in the form of a (hydro-)gel, suspension or solution) immediately before use, necessitating the addition of wetting or solvation (suspension) agents.

According to the present invention, the hemostatic composition is provided in dry form in the final container. In the dry form, degradation or inactivation processes for the components are significantly and appropriately reduced to enable storage stability.

The dry hemostatic compositions according to the present invention are usually reconstituted (re-hydrated) before use by contacting the dry composition with a pharmaceutically acceptable diluent. Such a pharmaceutically acceptable diluent may be part of the kit according to the present invention (together with the hemostatic composition). The diluent according to the present invention may be any suitable reconstitution medium ("reconstitution solution" or "re-hydration medium") for the dry hemostatic composition which allows suitable wetting of the dry composition. Preferably, the dry hemostatic composition is reconstituted into a hydrogel as a "ready-to-use" format.

Suitable diluents are pharmaceutically acceptable aqueous fluids, e.g. pharmaceutical grade de-ionized water (if all ionic or buffer components are already provided in the dry composition; "water-for-injection") or pharmaceutical grade aqueous solutions containing specific ions and/or buffers. Preferably, the diluent comprises a substance selected from the group consisting of NaCl, $CaCl_2$ and sodium acetate (or, of course, mixtures thereof).

For example, a suitable diluent comprises water for injection, and—independently of each other—50 to 200 mM NaCl (preferably 150 mM), 10 to 80 mM $CaCl_2$ (preferably 40 mM) and 1 to 50 mM sodium acetate (preferably 20 mM). Preferably, the diluent can also include a buffer or buffer system so as to buffer the pH of the reconstituted dry composition, preferably at a pH of 3.0 to 10.0, more preferred of 6.4 to 7.5, especially at a pH of 6.9 to 7.1.

According to a preferred embodiment, the diluent further comprises thrombin, preferably 10 to 1000 I.U. thrombin/ml, especially 250 to 700 I.U. thrombin/ml. Preferably, the hemostatic composition in this ready to use form contains 10 to 100.000 International Units (I.U.) of thrombin, more preferred 100 to 10.000 I.U., especially 500 to 5.000 I.U. The thrombin concentration in the ready-to-use composition is preferably in the range of 10 to 10.000 I.U., more preferred of 50 to 5.000 I.U., especially of 100 to 1.000 I.U./ml. The diluent is used in an amount to achieve the desired end-concentration in the ready-to-use composition. The thrombin preparation may contain other useful component, such as ions, buffers, excipients, stabilizers, etc.

These aqueous diluents may further contain other ingredients, such as excipients. An "excipient" is an inert substance which is added to the solution, e.g. to ensure that thrombin retains its chemical stability and biological activity upon storage (or sterilization (e.g. by irradiation)), or for aesthetic reasons e.g. color. Preferred excipients include human albumin and sodium acetate. Preferred concentrations of human albumin in the reconstituted product are from 0.1 to 100 mg/ml, preferably from 1 to 10 mg/m. Preferred sodium acetate concentrations are in the range of from 1 to 10 mg/ml, especially 2 to 5 mg/ml.

Preferably, the thrombin preparation contains human albumin. Preferred salts are NaCl and/or $CaCl_2$, both used in the usual amounts and concentrations applied for thrombin (e.g. 0.5 to 1.5% NaCl (e.g. 0.9%) and/or 20 to 80 mM $CaCl_2$ (e.g. 40 mM)).

In a preferred embodiment, the pharmaceutically acceptable diluent is provided in a separate container. This can preferably be a syringe. The diluent in the syringe can then easily be applied to the final container for reconstitution of the dry hemostatic compositions according to the present invention. If the final container is also a syringe, both syringes can be finished together in a pack. It is therefore preferred to provide the dry hemostatic compositions according to the present invention in a syringe which is finished with a diluent syringe with a pharmaceutically acceptable diluent for reconstituting said dry and stable hemostatic composition.

According to a preferred embodiment, the final container further contains an amount of a stabilizer effective to inhibit modification of the polymer when exposed to the sterilizing radiation, preferably ascorbic acid, sodium ascorbate, other salts of ascorbic acid, or an antioxidant.

According to another aspect, the present invention also provides a method for delivering a hemostatic composition according to the invention to a target site in a patient's body, said method comprising delivering a hemostatic composition produced by the process according to the present invention to the target site. Although in certain embodiments, also the dry composition can be directly applied to the target site (and, optionally be contacted with the diluent a the target site, if necessary), it is preferred to contact the dry hemostatic composition with a pharmaceutically acceptable diluent before administration to the target site, so as to obtain a hemostatic composition in a wetted form, especially a hydrogel form.

The present invention also refers to a finished final container obtained by the process according to the present invention. This finished container contains the combined components in a sterile, storage-stable and marketable form. The final container can be any container suitable for housing (and storing) pharmaceutically administrable compounds. Syringes, vials, tubes, etc. can be used; however, providing the hemostatic compositions according to the present invention in a syringe is specifically preferred. Syringes have been a preferred administration means for hemostatic compositions as disclosed in the prior art also because of the handling advantages of syringes in medical practice. The compositions may then preferably be applied (after reconstitution) via specific needles of the syringe or via suitable catheters. The reconstituted hemostatic compositions (which are preferably reconstituted to form a hydrogel) may also be applied by various other means e.g. by a spatula, a brush, a spray, manually by pressure, or by any other conventional technique. Administration of the reconstituted hemostatic composition to a patient by spraying is specifically preferred. Usually, the reconstituted hemostatic compositions according to the present invention will be applied using a syringe or similar applicator capable of extruding the reconstituted composition through an orifice, aperture, needle, tube, or other passage to form a bead, layer, or similar portion of material. Mechanical disruption of the compositions can be performed by extrusion through an orifice in the syringe or other applicator, typically having a size in the range from 0.01 mm to 5.0 mm, preferably 0.5 mm to 2.5 mm. Preferably, however, the hemostatic composition will be initially prepared from a dry form having a desired particle size (which upon reconstitution, especially by hydration, yields subunits of the requisite size (e.g. hydrogel subunits)) or will be partially or entirely mechanically disrupted to the requisite size prior to a final extrusion or other application step. It is, of course evident, that these mechanical components have to be provided in sterile form (inside and outside) in order to fulfill safety requirements for human use.

Another aspect of the invention concerns a method for providing a ready-to-use hemostatic composition comprising contacting a hemostatic composition produced by the process according to the present invention with a pharmaceutically acceptable diluent.

The present invention also concerns a kit comprising the dry and stable hemostatic composition according to the present invention in finished form and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles or catheters, extra vials or further wound cover means. Preferably, the kit according to the present invention comprises a syringe housing the dry and stable hemostatic composition and a syringe containing the diluent (or provided to take up the diluent from another diluent container). Preferably, these two syringes are provided in a form adapted to each other so that the diluent can be delivered to the dry hemostatic composition by another entry than the outlet for administering the reconstituted composition.

Therefore, a method for providing a ready to use form of a hemostatic composition according to the present invention, wherein the hemostatic composition is provided in a first syringe and a diluent for reconstitution is provided in a second syringe, the first and the second syringe are connected to each other, and the diluent is brought into the first syringe to produce a flowable form of the hemostatic composition; and optionally returning the flowable form of the hemostatic composition to the second syringe at least once, is a preferred embodiment of the present invention. This process (also referred to as "swooshing") provides a suitable "ready-to-use" form of the compositions according to the present invention which can easily and efficiently be made also within short times, e.g., in emergency situations during surgery. This flowable form of the hemostatic composition provided by such a method is specifically suitable for use in the treatment of an injury selected from the group consisting of a wound, a hemorrhage, damaged tissue, bleeding tissue and/or bone defects.

The invention is further described in the examples below and the drawing figures, yet without being restricted thereto.

FIG. 1 shows crosslinked gelatin mixed with 20 wt % of NETS-PEG hydrated with saline solution at neutral pH (Example 1) in a liver punch lesion model 5 min post application.

EXAMPLES

Example 1: Mixture Neutral

A mixture was prepared by mixing a specific amount of crosslinked gelatin particles with 20 wt % of NHS-PEG.

Typically, 6 g of gelatin particles in a 50 ml test tube were mixed with 1.2 g of NHS-PEG using end-over-end-mixer for at least 30 minutes in order to obtain a homogenous mixture of both components. From the mixture obtained, 0.96 g were weighted in a 5 ml syringe. As a diluent 3.5 ml of saline solution in a 5 ml syringe with female luer connector were used to hydrate the powder component before application to a bleeding site.

Hydration of the particulate component with the diluent was achieved by connection of both syringes and transforming the diluent to the syringe filled with the gelatin. In order to obtain a homogenous product, the content of the syringes was pushed back and forth at least 21 times. After hydration, a product obtained was allowed to hydrate for 2 minutes. A product obtained was applied to a bleeding wound using appropriate applicator tip attached to the syringe with a male luer.

Example 2: Mixture Basic

In order to obtain a faster reactive flowable hemostat the mixture as described in Example 1 was hydrated by using 3.5 ml of a basic buffer having pH of 9.5 as a diluent.

A product obtained was allowed to hydrate for 2 minutes and was applied to a bleeding wound.

Example 3: Mixture Acidic

In order to obtain a reactive flowable hemostat with prolonged stability the mixture as described in Example 1 was hydrated with 3.5 ml of saline solution having pH adjusted to 1.5 with 1M of HCl as a diluent.

A product obtained was allowed to hydrate for 2 minutes and was applied to a bleeding wound.

Example 4: In Vivo Study

A preparation of Example 1 was tested for hemostatic efficacy on heparinized animal (pig) in a punch or biopsy liver lesion. Each lesion in the series was topically treated with the product applied from the syringe through applicator tip. Moistened gauze was used to help approximate the test product to the lesion and the timer was started. A saline moistened approximation gauze was removed after 30 seconds and the degree of bleeding was assessed at 30 seconds, 1, 2, 5 and 10 minutes after the test articles were applied. Product saturated with blood but without active bleeding was scored as 0. Saline solution was used to irrigate the excess test articles away from the lesions after the 5 minutes assessment. Performance of selected formulations at 5 minutes assessment is shown in FIG. 1.

What is claimed is:

1. A method for producing a hemostatic composition in mixed dry form for treating a patient, the method comprising:
    placing, in a container, an amount of hemostatic biocompatible polymer in dry form, wherein the hemostatic biocompatible polymer is cross-linked gelatin, and wherein the cross-linked gelatin is present in particulate form having a median particle diameter within a range from 0.01 mm to 1.5 mm;
    placing, in the container, an amount of one hydrophilic polymeric component comprising reactive groups in dry form, wherein the reactive groups are electrophilic reactive groups, and wherein the one hydrophilic polymeric component comprising reactive groups is a polyethylene glycol; and
    mixing, in the container, the amount of the hemostatic biocompatible polymer in dry form and the amount of the one hydrophilic polymeric component comprising reactive groups in dry form to produce the hemostatic composition in mixed dry form, the hemostatic composition comprising a mixture of the amount of the hemostatic biocompatible polymer and the amount of the one hydrophilic polymeric component comprising reactive groups,
    wherein the amount of the hemostatic biocompatible polymer and the amount of the one hydrophilic polymeric component comprising reactive groups in mixed dry form are present in a ratio, wherein the ratio is of the hemostatic biocompatible polymer to the one hydrophilic polymeric component comprising reactive groups, wherein the ratio is in a range from 0.1% w/w to 50% w/w, and wherein the hemostatic composition does not include a second or further hydrophilic polymeric component with nucleophilic reactive groups.

2. The method according to claim 1, wherein the polyethylene glycol is pentaerythritolpoly(ethyleneglycol)ether tetrasuccinimidyl glutarate.

3. The method according to claim 1, wherein the ratio of the hemostatic biocompatible polymer to the one hydrophilic polymer component comprising reactive groups is in a range from 5% w/w to 40% w/w.

4. The method according to claim 1, further comprising hydrating an amount of the hemostatic composition in mixed dry form with an amount of a diluent to obtain a hydrated product.

5. The method according to claim 4, further comprising applying the hydrated product to a bleeding wound of the patient.

6. The method according to claim 4, wherein the diluent is neutral.

7. The method according to claim 6, wherein the diluent is a saline solution.

8. The method according to claim 6, further comprising applying the hydrated product to a bleeding wound of the patient.

9. The method according to claim 4, wherein the diluent is basic.

10. The method according to claim 9, wherein the diluent has a pH of 9.5.

11. The method according to claim 9, further comprising applying the hydrated product to a bleeding wound of the patient.

12. The method according to claim 4, wherein the diluent is acidic.

13. The method according to claim 12, wherein the diluent has a pH of 1.5.

14. The method according to claim 12, further comprising applying the hydrated product to a bleeding wound of the patient.

* * * * *